US012766281B2

(12) United States Patent
Komar et al.

(10) Patent No.: US 12,766,281 B2
(45) Date of Patent: Oct. 20, 2026

(54) SYSTEM FOR MONITORING TRACHEOSTOMY AIRFLOW

(71) Applicant: THE TRUSTEES OF THE STEVENS INSTITUTE OF TECHNOLOGY, Hoboken, NJ (US)

(72) Inventors: Franzisca Komar, San Diego, CA (US); Sally Shady, Upper Saddle River, NJ (US); Matthew Edward Iobst, Maywood, NJ (US); Julianna N. Ricci, Millersville, MD (US); Yanique Spigner, Paramus, NJ (US); Kenneth Poser, Upper Saddle River, NJ (US); Frank Castello, Montclair, NJ (US)

(73) Assignee: THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 1446 days.

(21) Appl. No.: 16/938,876

(22) Filed: Jul. 24, 2020

(65) Prior Publication Data

US 2021/0023317 A1 Jan. 28, 2021

Related U.S. Application Data

(60) Provisional application No. 62/879,065, filed on Jul. 26, 2019.

(51) Int. Cl.
*A61M 16/00* (2006.01)
*A61M 16/04* (2006.01)

(52) U.S. Cl.
CPC .... *A61M 16/0051* (2013.01); *A61M 16/0003* (2014.02); *A61M 16/0402* (2014.02);
(Continued)

(58) Field of Classification Search
CPC .......... A61M 16/0051; A61M 16/0003; A61M 16/0402; A61M 16/0465;
(Continued)

(56) References Cited

U.S. PATENT DOCUMENTS

| | | | | |
|---|---|---|---|---|
| 5,947,115 A * | 9/1999 | Lordo | A61M 16/0069 128/912 |
| 8,312,878 B2 * | 11/2012 | Orr | A61B 5/0833 128/204.22 |
| 2009/0107494 A1 * | 4/2009 | Freitag | A61M 16/00 128/207.14 |
| 2013/0253336 A1 * | 9/2013 | Haveri | A61M 16/0816 600/476 |
| 2017/0148467 A1 * | 5/2017 | Franklin | G10L 25/39 |

(Continued)

OTHER PUBLICATIONS

Trautlein D., "Single-use proximal flow sensors" Sensirion AG, Switzerland, https://www.sensirion.com/en/about%20us/newsroom/sensirion-specialist-articles/single-use-proximal-flow-sensors/.

(Continued)

*Primary Examiner* — Kendra D Carter
*Assistant Examiner* — Arielle Wolff
(74) *Attorney, Agent, or Firm* — Clark Hill PLC; Ralph Selitto; John K. Kim

(57) ABSTRACT

An adapter for use in conjunction with a tracheostomy tube and/or its attachments is disclosed. It is adapted to complement conventional tracheostomy tubes and monitor and measure an assortment of breathing parameters, through one or more sensors, such as thermistors, microphones and the like. In order to evaluate whether there is a problem in the patient's airway (e.g., an obstruction), the data from the sensors is compared. By incorporating an alarm system as part of, or in conjunction with, the present invention, healthcare providers can be better able to quickly react to potential problems in the patient's airway.

24 Claims, 5 Drawing Sheets

(52) U.S. Cl.
CPC .................. *A61M 16/0465* (2013.01); *A61M 2016/0021* (2013.01); *A61M 2205/3553* (2013.01); *A61M 2230/42* (2013.01); *A61M 2230/50* (2013.01)

(58) Field of Classification Search
CPC ............ A61M 2016/0021; A61M 2205/3553; A61M 2230/42; A61M 2230/50; A61M 16/1045; A61M 16/0463; A61M 16/0468; A61M 2016/0027; A61M 2016/0033; A61M 2205/3331; A61M 2230/40; A61M 2205/18; A61M 16/0816; A61M 16/024; A61M 2205/3334; A61M 2205/3368; A61M 2205/3375; A61M 2205/581; A61M 2205/583; A61M 2230/06; A61M 2230/30; A61M 16/021; A61M 16/022; A61M 16/026; A61B 5/0871; A61B 5/0878; A61B 5/6865
See application file for complete search history.

(56) References Cited

U.S. PATENT DOCUMENTS

| | | | | |
|---|---|---|---|---|
| 2018/0153440 | A1* | 6/2018 | Lee | A61M 16/0066 |
| 2018/0200466 | A1* | 7/2018 | Reinberg | F16M 11/12 |
| 2018/0272080 | A1* | 9/2018 | Porter | A61M 16/026 |
| 2019/0070376 | A1* | 3/2019 | Ferrer | A61M 16/0816 |
| 2020/0179629 | A1* | 6/2020 | Burgess | A61M 16/1095 |
| 2020/0297955 | A1* | 9/2020 | Shouldice | G16H 40/67 |
| 2021/0113796 | A1* | 4/2021 | Williams | A61M 16/0069 |

OTHER PUBLICATIONS

Wojsyk-Banaszak, Irena et al., "Evaluation of exhaled breath temperature (EBT) as a marker and predictor of asthma exacerbation in children and adolescents." Journal of Asthma. 2017: 54(7), doi: 10.1080/02770903.2017.1290104, https://www.ncbi.nlm.nih.gov/pubmed/28282228.

* cited by examiner

SYSTEM FOR MONITORING TRACHEOSTOMY AIRFLOW

CROSS-REFERENCE TO RELATED APPLICATION

This application claims priority to U.S. Provisional Patent Application Ser. No. 62/879,065 filed Jul. 26, 2019, the entire disclosure of which is incorporated herein by reference.

FIELD OF THE INVENTION

The present invention relates to real-tile sensing of breathing parameters, and more specifically, to a combination monitor and alert system for use with tracheostomy patients.

BACKGROUND OF THE INVENTION

The trachea is the physiological tube that allows the influx of air from the nose and mouth to reach the lung and is attached to the larynx superiorly, and the main bronchi inferiorly. The trachea is the only pathway that air can enter the body and reach the lungs, but it possesses a relatively small diameter. Because of this, the trachea can easily become obstructed. A tracheostomy is common when air cannot enter through the nose or mouth due to an upper airway obstruction, spinal cord injury, inability to clear secretion, or other situations requiring long-term mechanical ventilation.

A tracheostomy is a procedure performed to create a direct passageway for air through an incision and a tube placed in the throat. Each year, over 100,000 patients in the United States will require a tracheostomy; approximately 5,000 of these cases are pediatric patients. A large number of these patients (i.e., as many as 48%) may experience complications, such as obstructed airways caused by secretions and displacement of the tube. Unfortunately, patients with tracheostomies may have to undergo emergency surgery in the case of an undetected obstruction in the breathing tube leading to oxygen deprivation. Along with mucus and secretions, upper airway obstruction can involve growths and tumors that may be present in the airways of the nose and mouth (located above or within the trachea).

Obstructions routinely form within a tracheostomy tube from mucus secretions, and/or bacterial colonies. Early detection is key to prevent acute symptoms, among which are low oxygen saturation, elevated heart rates, and potential brain damage due to lack of oxygen. Prior devices do not directly measure exhalation and rely on signs of hypoxia to alarm. For example, pulse oximetry alerts when oxygen levels have begun dropping to low levels, meaning the patient has already been without oxygen for an extended period of time. ECG systems measure secondary effect of oxygen deprivation, and once changes in heart rate/pattern deviate from normal it may be too late to reverse. Early detection can prevent oxygen deprivation and possible brain damage. Oxygen deprivation can lead to brain damage, and can quickly become fatal within a time span of minutes. The aforementioned time spans are shortened for pediatric patients, who represent a more vulnerable population due to their inability to communicate when experiencing a life-threatening health complication.

Since occlusion of the tracheostomy tube by secretions can cause serious complications, it is imperative to detect occlusions as early as possible. Patients with tracheostomies requiring mechanical ventilation are monitored by the ventilator for signs of occlusions (i.e., obstructions), which signs include, for example, a sudden increase in ventilation pressure, very low tidal volume of respiratory gases, difficulty providing bag valve mask ventilation and the inability to pass a suction catheter. Paradoxically, as patients improve and are weaned from mechanical ventilation, their risk of death or disability increases due to obstruction of their tracheostomy. Once a patient with a tracheostomy has been removed from mechanical ventilation, there is no way to use the ventilator alarms to monitor the patient. Patients with tracheostomies who are not on mechanical ventilation must rely on secondary measures of safety such as pulse oximetry and/or ECG monitoring, both of which may detect complications after it is too late to intervene.

Traditionally, caretakers of patients with tracheostomies monitor the patients' vital signs using systems such as pulse oximetry and ECG as customary tools. However, these monitoring systems are limited as they monitor secondary effects of oxygen deprivation. Additionally, these devices work best when the patient is stationary. As motion artifact results in false alarms.

Pulse oximetry involves the measurement of absorption of light by hemoglobin resulting in the calculation of an oxygen saturation. Pulse oximetry works best when the subject is not moving and motion artifact often results in many false alarms. With the pulse oximetry device failing to obtain accurate readings, many false negatives and false positives are received, constituting an inherent lack of accuracy that is present using this system. Another shortcoming of this method is that it detects when the overall blood oxygen level has dropped significantly, which is a secondary effect of a tracheostomy obstruction or failure. By the time of detection using this approach, the blood oxygen level may have dropped significantly, meaning the patient will have been without sufficient oxygen for an extended period of time. Due to the short timeframe (i.e., minutes) available before a pediatric patient experiences brain damage due to oxygen deprivation, doctors have very little time to address the problem by the time a pulse oximeter detects it.

The next most common system utilized to monitor tracheostomy patients is an ECG (electrocardiography). This monitors the patient's heart rhythm. The resultant waveform of the heartbeat is displayed and if the rhythm is irregular and/or abnormal, the alarm will sound. This, again, only monitors for the secondary effect due to the patient's inability to breathe. When blood oxygen levels have dropped, the heart rate is then affected. Therefore, the ECG also gives very little time for the doctors to react to the drop in the oxygen levels in the blood.

SUMMARY OF THE INVENTION

The present invention is a combination monitor and alert system that may be used by tracheostomy patients who have been weaned off a ventilator and transitioned to long-term care facilities or home care. The invention has utility as an early detection system for monitoring the airflow through the tracheostomy tube of outpatients to improve quality of life and prevent oxygen deprivation. In use, the present invention functions to alert a caregiver, within a 20 second window, of the onset of an abnormal breathing condition in a patient. In an embodiment, the invention includes a tracheostomy tube attachment, and a wearable component designed to fit on the tracheostomy tube patient. The wearable component can include means for receiving and/or processing data and may be worn, for instance, on the patient's arm.

The present invention monitors the airway of tracheostomy patients for early detection of obstruction in the airway of the tracheostomy tube. In an embodiment, airflow is monitored using a dual-function microphone/pressure transducer and a thermistor sensor. Through the use of a dual sensor system, the device continuously monitors airflow from the tracheostomy tube and detects abnormalities within a patient's breathing pattern. If there is an obstruction, the device will detect the size and severity of the obstruction. Through the use of at least two sensors, four or more vital signs can be measured. Such measurements can include breath rate, breath pattern, effort in breathing (i.e., sound power), and flow rate (i.e., air velocity) and can be detected from the observed airflow and temperature. All of these vital signs are used to cause the device to issue an alert when an obstruction or severe irregularity in the patient's breathing is detected. The use of two sensors together offers the ability to compensate for the thermistor potentially under-responding and the microphone over-responding to stimuli. This will reduce the number of false positives the device may give off, making it more reliable in its everyday use.

An object of the present invention is to monitor pediatric tracheostomy patients to ensure normal breathing patterns and determine severity of obstructions that build up in the patients' tracheostomy tube.

Another object of the present invention is to monitor adult patients with tracheostomy tubes to identify the severity of obstruction and prevent full obstruction and oxygen deprivation.

A further object of the present invention is to collect real-time data for patients' peak expiratory flow rates to thereby further research for tracheostomy patients.

Yet another object of the present invention is to provide lung and cardiac chest sound monitoring for early detection of cardiothoracic conditions.

BRIEF DESCRIPTION OF FIGURES

For a more complete understanding of the present disclosure, reference is made to the following drawings, in which.

DETAILED DESCRIPTION OF EXEMPLARY EMBODIMENTS

Figure 1A:
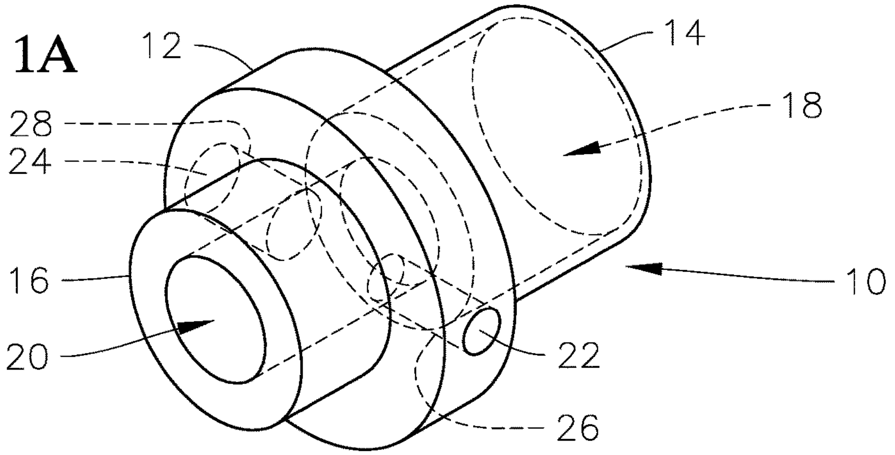
FIG. 1A is a perspective view of an attachment adapter constructed in accordance with an embodiment of the present invention in which the attachment adapter is configured for use with a tracheostomy tube, various internal features of the attachment adapter being shown in phantom to facilitate consideration and discussion.
Figure 1B:
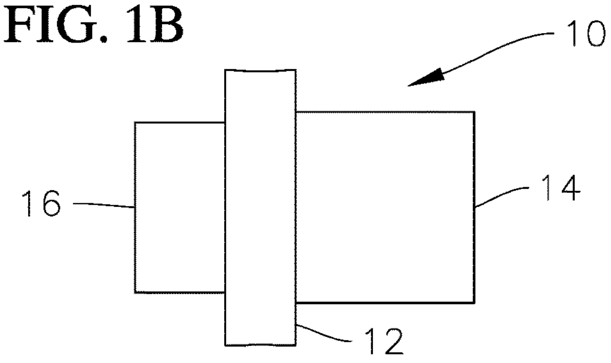
FIG. 1B is a top plan view of the attachment adapter of FIG. 1A, the bottom plan view of the attachment adapter being identical to FIG. 1B.
Figure 1C:
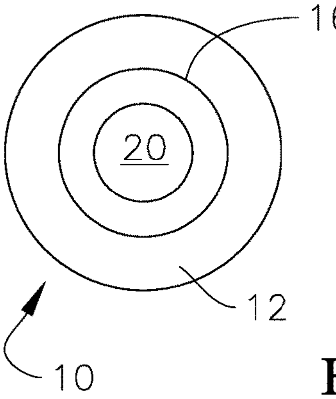
FIG. 1C is an anterior end view of the attachment adapter of FIG. 1A.

Referring initially to FIGS. 1A-1F, there is shown a retrofittable attachment adapter 10 having a circular collar 12 projecting outwardly from an outer surface of the adapter 10. The attachment adapter 10 also includes a proximally located (relative to a patient, such as the patient depicted in FIG. 4) tubular female end 14 and a distally located (relative to a patient, such as the patient shown in FIG. 4) tubular male end 16, whose functions will be more fully described hereinbelow. A wide proximal channel 18 extends through the attachment adapter 10 from its tubular female end 14 in the direction of the tubular male end 16. Within the adapter 10, wide proximal channel 18 narrows into a distal central channel 20, which channel 20 ends at the tubular male end 16.

Figure 1D:
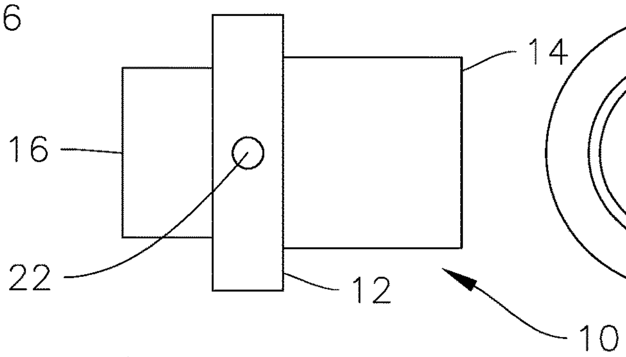
FIG. 1D is a left side elevational view of the attachment adapter of FIG. 1A.
Figure 1E:
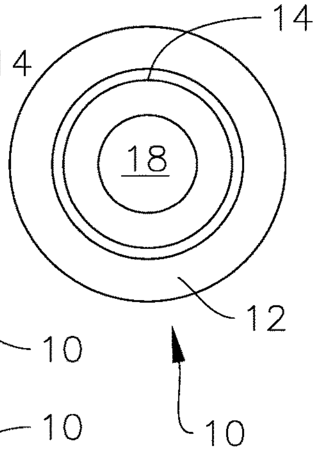
FIG. 1E is a posterior end view of the attachment adapter of FIG. 1A.
Figure 1F:
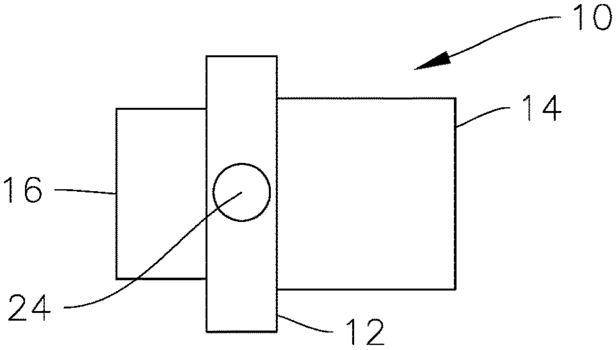
FIG. 1F is a right side elevational view of the attachment adapter of FIG. 1A.

The attachment adapter 10 is sized, shaped and/or otherwise configured to house a thermistor 22 and a multifunctional microphone 24. More particularly, the attachment adapter 10 houses thermistor 22 and microphone 24 such that the adapter 10 is compatible with current tracheostomy tube attachments. As shown in FIGS. 1A, 1D and IF, the thermistor 22 and the microphone 24 are housed in mounting cavities 26, 28, respectively, provided on diametrically opposed sides of the collar 12. The thermistor 22 and the microphone 24 may be used in accordance with the present invention to collect various data types. A suitable thermistor is manufactured by Vishay Dale as Part No. NTHS0402N02N1202JE, while a suitable microphone is manufactured by CUI Inc., as Part No. CMC-6036-40L1, 100.

In an embodiment, thermistor 22 may be associated with the attachment adapter 10 for the purpose of determining the breath rate of patients via temperature. The thermistor 22 may operate in conjunction with microphone 24, which can be multi-functional as indicated above. In an embodiment, the microphone 24 can have three main audio-based functionalities to directly or indirectly determine breath sounds, sound power level (to determine effort in breathing), and air velocity. Air velocity may, in turn, be used to determine Peak Expiratory Flow Rates (PEFR). To these ends, the microphone 24 continuously measures calculated pressure (p), which is calculated by dividing the received sound pressure signal by the sensitivity of the sensing microphone 24.

As indicated above, the attachment adapter 10 is configured to press fit to conventional tracheostomy tubes and conventional attachments therefor. In one embodiment, the adapter 10 can be placed along a 15 mm adapter 3*o* of tracheostomy tube 32 and attached thereto in a manner similar to a standard tracheostomy tube attachment. This manner of assembly permits thermistor 22 and microphone 24 to be positioned generally perpendicular to the airflow through central channel 20, whereby the thermistor 22 and the microphone 24 are capable of detecting airflow coming from the tracheostomy tube 32. In one embodiment, a neck flange 34 associated with the tracheostomy tube 32 equips the adapter 10 for use with pediatric patients by helping position the tracheostomy tube 32 flush to the patient's neck. In an embodiment, the proximal channel 18 at the female end 14 of adapter 10 is configured to receive the 15 mm adapter 30 associated with the tracheostomy tube 32.

The attachment adapter 10 is also seen in combination with a heat and moisture exchanger attachment 36, which functions to reduce secretions. Various conventional attachments for tracheostomy tubes include, in addition to a heat moisture exchanger attachment 36, a Passy-Muir valve attachment (not shown), which allows patients to speak. The present invention is specifically adapted for use in combination with such attachments, as they can be placed on the distally located male end 16 of the adapter 10. By way of example, an auxiliary female end 38 of the heat and moisture exchanger attachment 36 can mate with tubular male end 16 of adapter 10.

Figure 2:
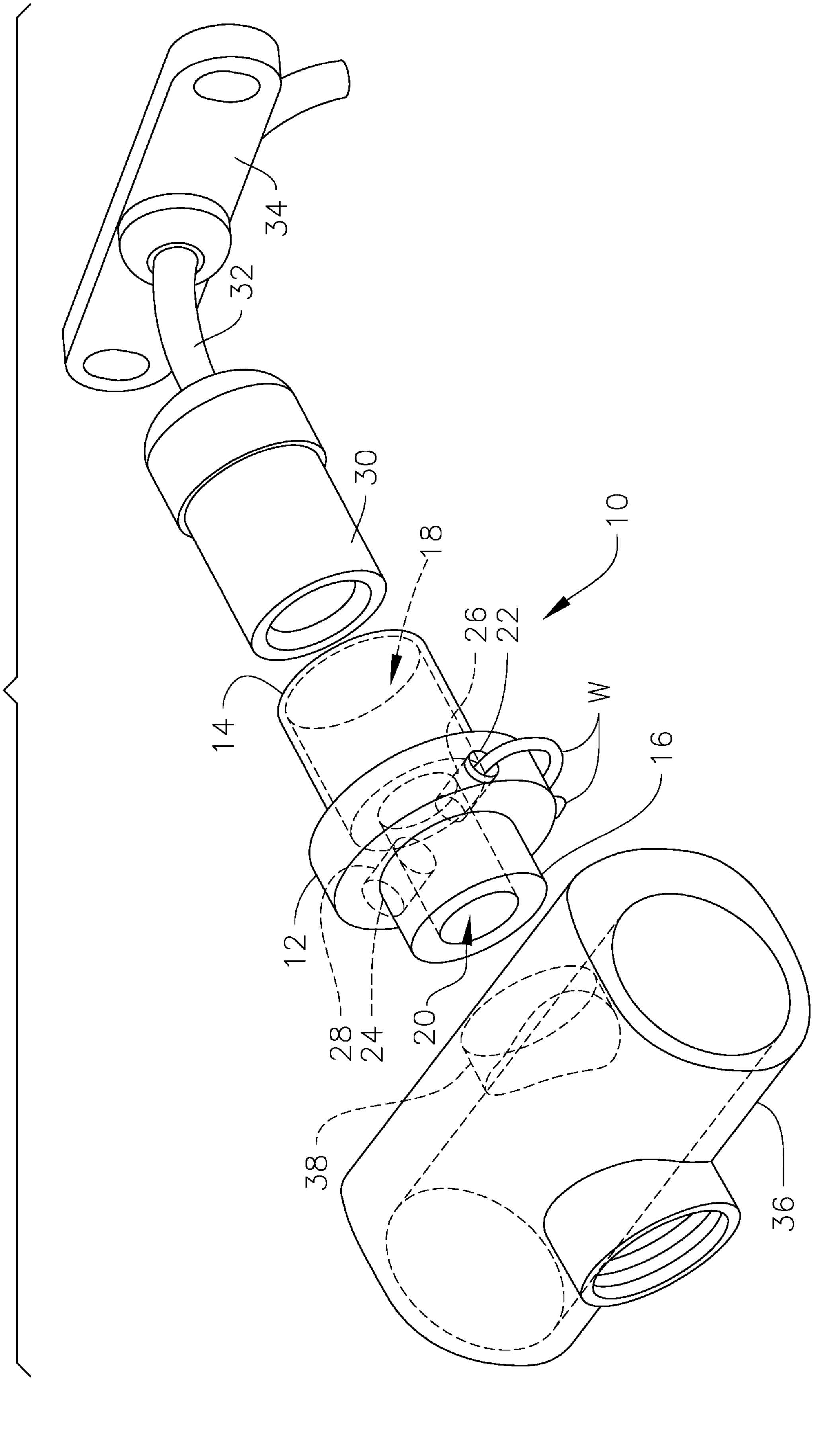
FIG. 2 is an exploded perspective view of the attachment adapter of FIGS. 1A-1F, shown in combination with a conventional pediatric tracheostomy tube and a conventional heat and moisture exchanger attachment, various features of the combination being shown in phantom to facilitate consideration and discussion.
Figure 3:
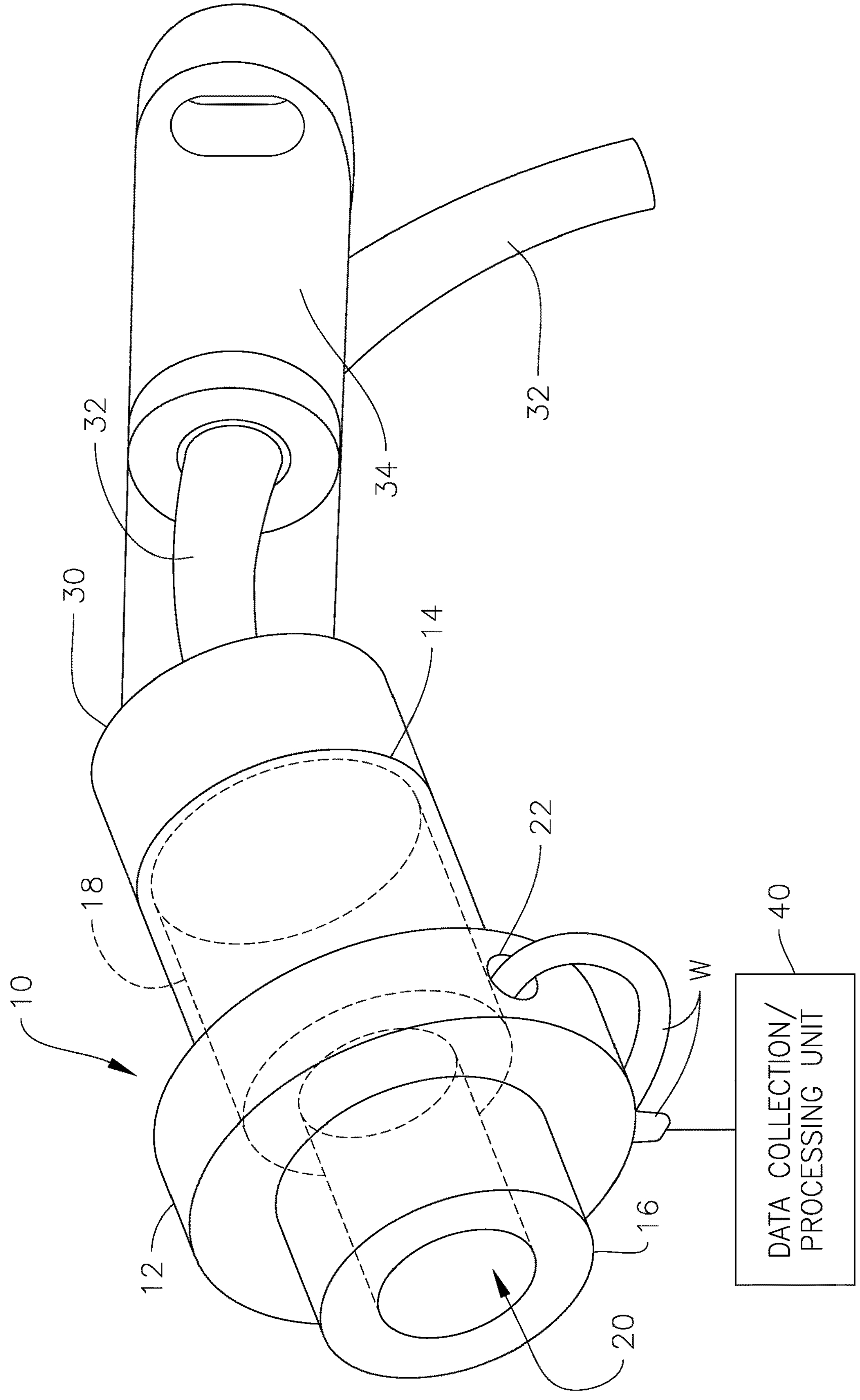
FIG. 3 is a perspective view of the attachment adapter of FIG. 2, shown assembled to the pediatric tracheostomy tube of FIG. 2, various features of the assembly being shown in phantom to facilitate consideration and discussion.
Figure 4:
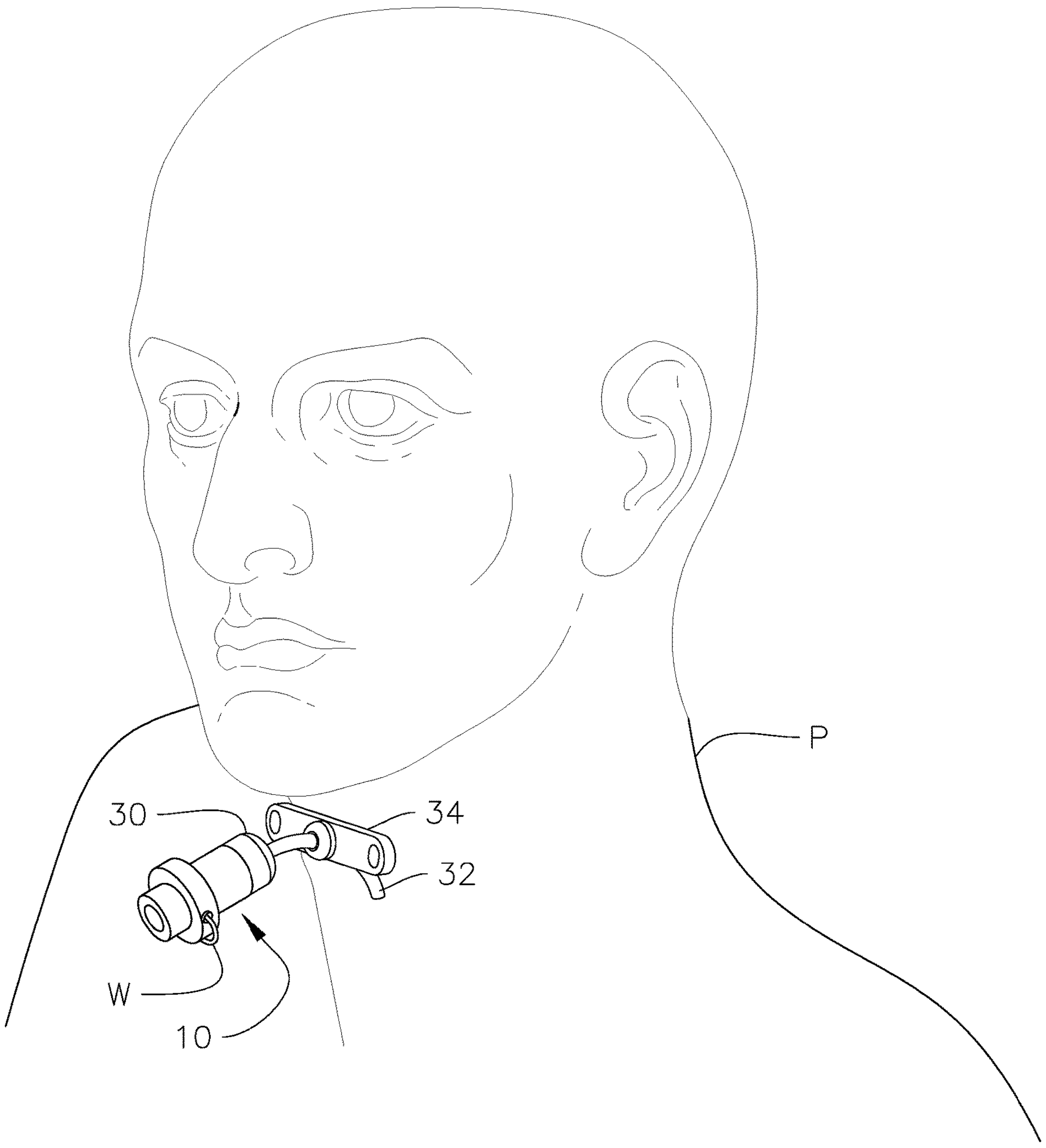
FIG. 4 is a perspective view showing the assembly of FIG. 3 in use on an individual patient.

Referring now to FIG. 4, the combination of FIGS. 2 and 3 is shown interfacing with a neck of a patient P. In an embodiment, the thermistor 22 and microphone 24 of adapter 10 are coupled via wires W to a data collection system, processor and/or user interface (e.g., data collection/processing unit 40 in FIG. 3), which may be contained in a separate housing unit as a wearable component on the patient P, or placed elsewhere, such as a location remote from the patient P.

Figure 5:
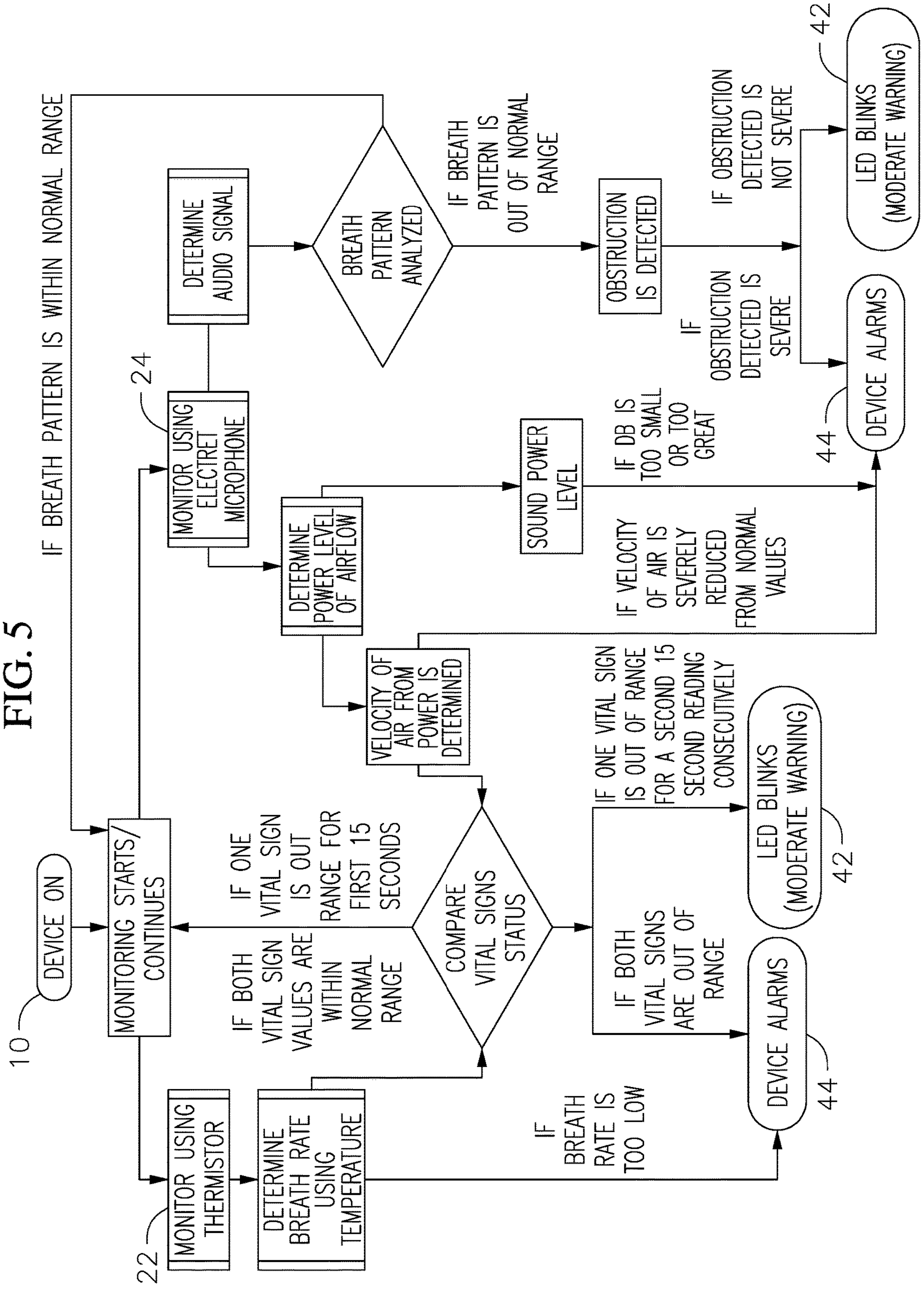
FIG. 5 is a schematic diagram of an exemplary embodiment of a process for implementing the present invention.

FIG. 5 is a flow diagram illustrating an exemplary implementation and use of the attachment adapter 10. Thermistor 22 and microphone 24 monitor various parameters (e.g., breath rate and sound power level) and they are then compared to determine if the airway is obstructed and to what degree. In one embodiment, the adapter 10 can determine whether or not an obstruction is present within the tracheostomy tube 32. Based on the data received, a warning LED 42 may flash or an alarm 44 may sound in the user interface (e.g., one connected to the data collection/processing unit 40 shown in FIG. 3).

Advantageously, dual sensor systems, such as the one employed by the adapter 10 allow for consistent monitoring, which therefore reduces the number of false alarms. Such dual sensor systems serve as a failsafe; for example, in an embodiment, the sensors compare readings and the alarm 44 is sounded only if both values are abnormal. For example, when the sensors of such dual sensor systems detect a variation in the volumetric flow rate from normal readings for a prolonged period (e.g., twenty seconds or more), the alarm 44 may be triggered to alert a caregiver that there is an obstruction or cessation of breathing.

In use, the attachment adapter 10 continuously monitors tracheostomy patients for indications of airway obstruction using a dual sensor system. Breath rate, breath sounds, effort in breathing, and air velocity as discussed below, may be measured by the sensors (e.g., thermistor 22 and microphone 24) in order to indicate the presence of an obstruction.

The concurrent use of two sensors in combination offers the ability to compensate for the thermistor 22 potentially under-responding and the microphone 24 over-responding to stimuli. The adapter 10 therefore reduces the number of false positives it may give off, making the adapter 10 more reliable in its everyday use while also allowing it to monitor four or more of a patient's vital signs simultaneously. By measuring and interpreting four or more parameters, the number of false positives and false negatives can be reduced. Breathing rate patterns can be continuously recorded, and the degree of airway obstruction can be determined within 20 seconds, for example.

Secondary physiological parameters such as heart rate, and Peak Expiratory Flow Rates (PEFR) may also be measured by the adapter 10. As such, additional functionalities of the adapter 10 can include detecting heart rate, blood pressure and peak expiratory flow rates.

The functionalities of each of the sensors described above (i.e., the thermistor 22 and the microphone 24) are outlined in the following examples (i.e., Examples 1-4).

Example 1—Thermistor Functionality

The use of the thermistor 22 in determining breath rates is based on thermodynamic principles which assume that air leaving the human body will be warmed to a value close to 'normal' body temperature, as a result of the energy exchange while the air passes through the respiratory system. The actual circuit analysis required to get the thermal values from raw sensor output uses electrical engineering principles. The temperature value will be determined using the Steinhart-Hart equation, as well as a Kelvin to Celsius conversion. The Steinhart-Hart equation models the value of the resistance in a semi-conductor (i.e., thermistor 22) at various temperatures C1, C2, C3 (in Kelvin):

$$Tk = \frac{1}{C1 + C2(\ln R) + C3(\ln R)^3}.$$

Temperature in Celsius ($T_C$) can be converted to temperature in Kelvin ($T_K$) with the formula TC=TK−273.15. From this, the breath rate of the patient can be obtained. The thermistor 22 will begin taking readings and continuously compare the readings to normal range values (based on patient age) as seen in Table 1 below.

TABLE 1

Normal Breath Rate Readings

| Age Range | Breaths Per Minute |
|---|---|
| Up to 6 Months | 30-60 |
| 6-12 Months | 24-30 |
| 1-5 Years | 20-30 |
| 6-12 Years | 12-20 |
| 12-59 Years | 12-16 |
| 60+ Years | 16-25 |

Example 2—Determining Peak Expiratory Flow Rates (PEFR) Based on Air Velocity Measurements Detected Via Multi-Functional Microphones Like Microphone 24

The first function derived from the microphone 24 is determining air velocity for the patient. This can be used to obtain an approximate PEFR in real time. In an embodiment, if PEFR is 80-100% of the normal vital rate, it will be considered in range. If PEFR is within 60-80% of normal values it will be considered out of range. If PEFR is less than 60% of normal vital values, an alarm will be provided immediately. The velocity of air (v) can be determined from the microphone's pressure readings (p) with the formula v=I/p, where I is intensity calculated by the formula I=P/A. The air velocity may then be converted into PEFR by first calculating expiratory flow rate (EFR): EFR=Av.

The air velocity and thermistor vital signs will be compared to one another every 15 seconds. If both vital signs are within normal ranges the device will continue to monitor. The device will continue to monitor even if one of the signs is abnormal, but after thirty consecutive seconds of abnormal readings the device provide a warning (e.g., by blinking the LED 42). If both vital signs are abnormal, an alarm (e.g., by actuating alarm 44) will be immediately given, indicating an obstruction or other vital issue.

Example 3—Determining Effort in Breathing Based on Sound Power Levels Detected Via Multi-Functional Microphones Like Microphone 24

Sound power measurements may be derived from the raw microphone signal to determine effort in breathing from the patient via determination of a sound power level (SPL). A processor, whether integral with the device or separately housed, calculates sound power through a logarithmic equation which converts a raw voltage signal into a power value (P):

$$P = \frac{Ap^2}{\rho c}\cos(\theta),$$

where c is the velocity of sound constant, ρ is density of the medium (i.e., air), A is the cross-sectional area of the channel 20 of the inventive adapter 10, and θ is the angle between the direction of propagation of measured sound and a normal to a reference surface. A power level equation is then used to convert the power values into a decibel level (i.e., SPL), which is used to indicate the effort in breathing:

$$SPL = 10\log\frac{P}{P0}$$

for a given reference sound power $P_o$. The sound power sensor will trigger an alarm when the patient's breath sound power levels indicate too little effort detected (little to no airflow), as well as when breath sound levels are too high, indicating an obstruction in the tracheostomy tube. By indicating when sound levels are too low, the device will alarm when the tracheostomy tube has inappropriate airflow due to being removed or misplaced.

Example 4—Determining Breath Sounds Based on Audio Signals Detected Via Multi-Functional Microphones Like Microphone 24

The third function of the microphone 24 will be to determine the tracheal breath sounds of the patient. A notch filter will be applied to the raw signals obtained to remove any 60 Hz noise associated with common electronic devices such as lights and simple electronics. Peak detection analyzes the filtered signal over a five second period and then indicates the number of positive and negative peaks present in the sample (as well as their values). A normal range for the peak values will be determined based on repetitive testing, this will be represented as the range A-B with A less than B. The number of peak values that falls within the range of A-B (normal breath patterns) will be compared to the number of peaks that are less than A or greater than B (abnormal breath patterns). An obstruction will be indicated in the tracheostomy tube within 15 seconds if the quantity of peak values representing abnormal breath patterns is greater than the quantity of peak values representing normal breath patterns. The breath patterns so determined may also be used to indicate the level of obstruction, allowing the device to alert to the severity of the obstruction.

In conclusion, the attachment adapter 10 is a Class II, disposable, single use medical device which is attachable to conventional tracheostomy tubes and can be used to monitor other conditions that result from obstructed airways. The adapter 10 can, for example, be 3D printed and, by way of further example, it may be made out of PVC to provide durability, biocompatibility and potential reduction in cost. Furthermore, the adapter 10 of the present invention is portable and lightweight, enabling patients to leave hospitals or other long-term care facilities.

It will be understood that the embodiments described hereinabove are merely exemplary and that a person skilled in the art may make many variations and modifications without departing from the spirit and scope of the present invention. All such variations and modifications are intended to be included within the scope of the invention as defined in the appended claims.

The invention claimed is:

1. A method for monitoring a flow rate of air passing through a tracheostomy tube in use on a tracheostomy patient who is not on a ventilator, said method comprising the steps of:

(a) providing said tracheostomy tube with an adapter having a tubular body, said body having a first end proximal to and connected to said tracheostomy tube, a second end distal to said tracheostomy tube, a collar disposed about said body and integral therewith, said collar located between said first and second ends of said body, and a channel extending through said body from said first end thereof to said second end thereof, a thermistor housed in said collar and adapted to make breath rate measurements of said patient via temperature-based sensing of air flowing from said tracheostomy tube through said channel, and a microphone housed in said collar and adapted to make pressure-based velocity measurements of air flowing through said channel from said tracheostomy tube;

(b) attaching said tracheostomy tube to said patient;

(c) measuring, via said thermistor and for a predetermined time period, the breath rate of said patient based on the temperature of the air flowing from said tracheostomy tube;

(d) measuring, via said microphone and for said predetermined time period, the velocity of the air flowing from said tracheostomy tube based on the pressure of the air flowing from said tracheostomy tube, step (d) being performed simultaneously with step (c);

(e) comparing the breath rate measured in step (c) to a normal breath rate value and determining whether the measured breath rate is normal or abnormal;

(f) converting the air velocity measured in step (d) to an approximate peak expiratory flow rate;

(g) comparing the approximate peak expiratory flow rate to a normal vital peak expiratory flow rate value and determining whether the approximate peak expiratory flow rate is normal or abnormal;

(h) determining a degree of obstruction of said tracheostomy tube by measuring a breathing effort of said patient based on sound power levels calculated from the pressure of the air flowing from said tracheostomy tube and the breath rate calculated from the temperature of the air flowing from said tracheostomy tube; and (i) producing an alarm if the degree of obstruction of said tracheostomy tube and/or both the measured breath rate and the approximate peak expiratory flow rate are determined to be abnormal for said predetermined time period.

2. The method of claim 1, wherein the breath rate measured by said thermistor is measured over a predetermined time period during which the measured breath rate is compared to the normal breath rate value.

3. The method of claim 2, wherein said normal breath rate value is dependent upon an age of the tracheostomy patient.

4. The method of claim 2, wherein the velocity of air measured by said microphone is measured over said predetermined time period during which the air velocity measurement is used to obtain an approximate peak expiratory flow rate which is then compared to a normal vital peak expiratory flow rate value.

5. The method of claim 4, wherein an alarm signals when said approximate peak expiratory flow rate is a certain percentage below said normal vital peak expiratory flow rate value.

6. The method of claim 4, wherein said adapter is used in combination with a processor adapted to determine the degree of obstruction of said tracheostomy tube and to determine when said measured breath rate is abnormal compared to said normal breath rate value and to determine when said approximate peak expiratory flow rate is abnormal compared to said normal vital peak expiratory flow rate value.

7. The method of claim 6, wherein said processor triggers an alarm if both said measured breath rate and said approximate peak expiratory flow rate are determined to be abnormal for said predetermined time period.

8. The method of claim 7, wherein said processor is located remote from said device and is configured for wireless communication therewith.

9. The method of claim 6, wherein said processor is included in a wearable component worn by the patient.

10. The method of claim 6, wherein said processor is configured to determine said degree of obstruction based on said breath rate measurements, and sound power levels calculated from voltage signals produced by said microphone.

11. The method of claim 4, wherein said microphone measures breath sounds of the tracheostomy patient based on audio signals.

12. The method of claim 11, wherein an alarm signals when said breath sounds are outside a predetermined normal range.

13. The method of claim 4, wherein said microphone measures breathing effort of the tracheostomy patient based on sound power levels calculated from voltage signals produced by said microphone.

14. The method of claim 13, wherein an alarm signals when said sound power levels are too high or too low.

15. The method of claim 1, wherein said first end includes a female mating end adapted to receive said tracheostomy tube, and wherein said second end-comprises a male mating end.

16. The method of claim 15, wherein said male mating end of said adapter is configured for selective mating with a retrofittable tracheostomy tube attachment selected from a group including a passy muir valve attachment and a heat and moisture exchanger attachment.

17. The method of claim 15, wherein said female mating end is adapted to press-fit to said tracheostomy tube.

18. The method combination of claim 1, wherein said thermistor and said microphone are mounted to said collar such that said thermistor measures the breath rate of the tracheostomy patient based on the temperature of the air flowing through said channel of said adapter from the tracheostomy tube and such that said microphone measures the velocity of the air flowing through said channel of said adapter from said tracheostomy tube.

19. The method of claim 1, further comprising the step of attaching said adapter to the tracheostomy tube such that air flowing through the tracheostomy tube from the tracheostomy patient can flow through said adapter.

20. The method of claim 1, wherein said adapter is disposable.

21. The method of claim 1, wherein said adapter is portable.

22. The method of claim 1, further comprising a data processing unit, communicatively coupled to said adapter and configured to simultaneously process data from said thermistor and said microphone.

23. The method of claim 1, wherein said thermistor is positioned perpendicular to a longitudinal axis of said channel.

24. The method of claim 1, wherein said microphone is positioned perpendicular to a longitudinal axis of said channel.

* * * * *